US010330911B2

(12) United States Patent
Roul et al.

(10) Patent No.: US 10,330,911 B2
(45) Date of Patent: Jun. 25, 2019

(54) METHOD FOR CONTROLLING A PLURALITY OF FUNCTIONAL MODULES INCLUDING A MULTI-WAVELENGTH IMAGING DEVICE, AND CORRESPONDING CONTROL SYSTEM

(71) Applicants: CNRS—Centre National de la Recherche Scientifique, Paris (FR); UNIVERSITE DE RENNES 1, Rennes (FR)

(72) Inventors: Julien Roul, Rennes (FR); Marc Tramier, Rennes (FR); Jacques Pecreaux, Rennes (FR)

(73) Assignees: CNRS—CENTRE NATIONAL DE LA RECHERCHE SCIENTIFIQUE, Paris (FR); UNIVERSITE DE RENNES 1, Rennes (FR)

( * ) Notice: Subject to any disclaimer, the term of this patent is extended or adjusted under 35 U.S.C. 154(b) by 142 days.

(21) Appl. No.: 15/300,126

(22) PCT Filed: Mar. 23, 2015

(86) PCT No.: PCT/EP2015/056157
§ 371 (c)(1),
(2) Date: Sep. 28, 2016

(87) PCT Pub. No.: WO2015/144650
PCT Pub. Date: Oct. 1, 2015

(65) Prior Publication Data
US 2017/0139196 A1    May 18, 2017

(30) Foreign Application Priority Data
Mar. 28, 2014  (FR) .................................... 14 52766

(51) Int. Cl.
*G02B 21/36*   (2006.01)
*G02B 21/00*   (2006.01)
(Continued)

(52) U.S. Cl.
CPC ....... *G02B 21/365* (2013.01); *G02B 21/0044* (2013.01); *G02B 21/0076* (2013.01);
(Continued)

(58) Field of Classification Search
None
See application file for complete search history.

(56) References Cited

U.S. PATENT DOCUMENTS 7,024,250 B2    4/2006   Graf et al.
2005/0248764 A1   11/2005   Tanemura et al.
(Continued)

FOREIGN PATENT DOCUMENTS

EP    1388397 A2    2/2004

OTHER PUBLICATIONS

Written Opinion of the International Searching Authority dated Mar. 23, 2015, for corresponding International Application No. PCT/EP2015/056157, filed Mar. 28, 2014.
(Continued)

*Primary Examiner* — Heather R Jones
(74) *Attorney, Agent, or Firm* — David D. Brush; Westman, Champlin & Koehler, P.A.

(57) ABSTRACT

A method is proposed for driving a plurality of functional modules included in a multi-wavelength microscopy imaging device. The device includes at least one first functional module and a second functional module, adapted respectively to performing a first function and a second function. The method includes at least one iteration of the acts of: sending a first driving signal to the second functional module when the first functional module has performed said
(Continued)

first function; the second functional module triggers the function upon reception of the first driving signal; sending a second driving signal to the first functional module when the second functional module has performed said second function; the first functional module triggers said first function upon reception of the second driving signal.

11 Claims, 6 Drawing Sheets

(51) Int. Cl.
    *G02B 21/16*      (2006.01)
    *G05B 19/042*      (2006.01)
    *G05B 19/418*      (2006.01)
    *G02B 21/26*      (2006.01)
    *G01N 21/64*      (2006.01)

(52) U.S. Cl.
    CPC ............. *G02B 21/16* (2013.01); *G02B 21/26* (2013.01); *G05B 19/042* (2013.01); *G05B 19/0421* (2013.01); *G05B 19/41815* (2013.01); *G01N 21/6458* (2013.01); *G05B 2219/33278* (2013.01); *Y02P 90/08* (2015.11)

(56) References Cited

U.S. PATENT DOCUMENTS

2008/0315136 A1* 12/2008 Ryu ...................... G02B 21/16
                                                                                     250/580
2013/0242382 A1* 9/2013 Komuro ................ G02B 21/16
                                                                                      359/363

OTHER PUBLICATIONS

International Search Report dated Jul. 2, 2015 for corresponding International Application No. PCT/EP2015/056157, filed Mar. 23, 2015.
Meier, Hans: "Verteilte, Kooperative Steuerung Maschinennaher Ablaufe", Institut fur Werkzeugmaschinen and Betriebswissenschaften Technische Universitat Munchen Internet, May 10, 2001, pages Front p. 30, XP002728551.
International Preliminary Report on Patentability and English translation of the Written Opinion of the International Searching Authority dated Oct. 4, 2016, for corresponding International Application No. PCT/EP2015/056157, filed Mar. 28, 2014.

* cited by examiner

METHOD FOR CONTROLLING A PLURALITY OF FUNCTIONAL MODULES INCLUDING A MULTI-WAVELENGTH IMAGING DEVICE, AND CORRESPONDING CONTROL SYSTEM

1. CROSS-REFERENCE TO RELATED APPLICATIONS

This Application is a Section 371 National Stage Application of International Application No. PCT/EP2015/056157, filed Mar. 23, 2015, the content of which is incorporated herein by reference in its entirety, and published as WO 2015/144650 on Oct. 1, 2015, not in English.

2. FIELD OF THE INVENTION

The invention relates to the field of imaging systems and can be applied for example in multi-wavelength or multi-color microscopy.

More specifically, the invention relates to a technique for controlling a plurality of functional modules (or blocks) contained in a microscopy imaging device.

The invention can be applied especially but not exclusively in the field of the imaging of biological samples for the analysis of dynamic processes in cell biology, requiring the use of a system of multi-wavelength fluorescence microscopy.

3. TECHNOLOGICAL BACKGROUND

We shall strive more particularly below in this document to describe the problems and issues in the field of imaging in multi-wavelength microscopy that the inventors of the present patent application have faced. In general, a multi-wavelength imaging device images a sample subjected to different excitation wavelengths. The invention is of course not limited to this particular field but is of interest in any driving technique implemented in a system of imaging in microscopy that has to cope with similar or proximate problems and issues.

3.1 Context of the Invention

The Institute of Genetics and Development of Rennes (IGDR) is developing an imaging device based on multi-wavelength fluorescence microscopy to study the dynamics of biochemical activities (such as cell metabolism) or biophysical activities (such as the dynamics of cell division) in living samples. This imaging device corresponds to high demand from biologists wishing to use a technique of in vivo space/time analysis of biological events and thus access functional information on the observed samples.

Figure 1:
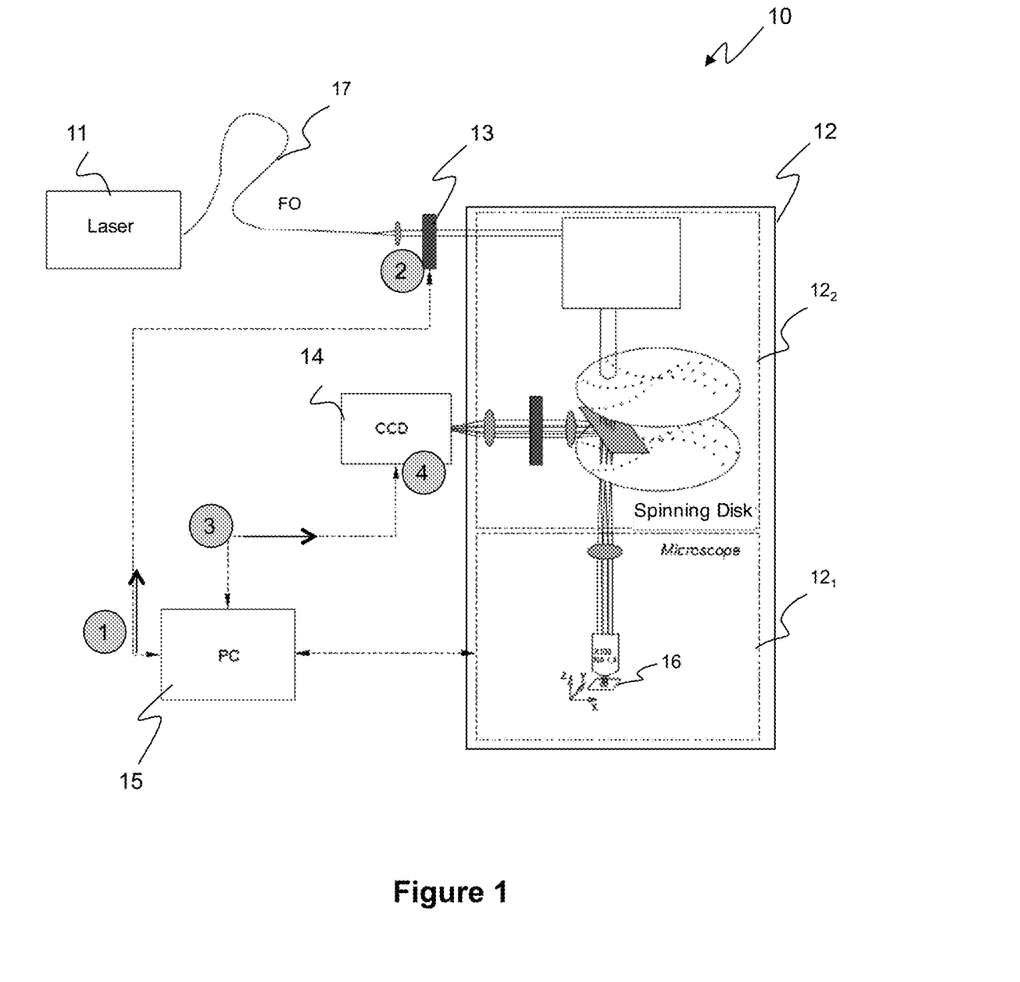
FIG. 1, already described with reference to the prior art, represents an example of a multi-wavelength multifocal imaging device known in the prior art.

FIG. 1 illustrates an example of a traditional multi-wavelength imaging device 10 comprising a laser light source 11 coupled with a multifocal microscope 12 by means of an optical fiber 17 (denoted as "FO" in the figure). The light source 11 produces a white laser excitation light (also called a "supercontinuum") in the form of impulses of the order of a few picoseconds intended to illuminate the sample 16 to be observed. The multifocal microscope 12 is formed by an imaging module $12_1$ cooperating with a rotating device $12_2$ confocal with the plane of the sample, also commonly called a "spinning disk". The device 10 furthermore comprises a wavelength-selection module 13 that takes the form of a mobile disk provided with a set of optical interference filters (low-pass or bandpass filters). This disk with optical filters is mounted so as to be rotationally mobile about a rotation axis enabling the selection of a wavelength or a desired range of wavelengths as a function of the optical filter presented. The images are acquired done by means of an image-capturing module 14, for example a CCD (Charge-Coupled Device) or CMOS (Complementary Metal Oxide Semiconductor) sensor type camera.

To carry out a multi-wavelength acquisition, each of the functional modules (or blocks) described above is driven by means of one-way commands sent out in succession by a driving software program stored in central processing unit 15 (denoted in the figure as PC for "personal computer"). These modules are however capable of sending back information on their state or configuration following an interrogation through the software and the PC.

The functioning of the present-day multi-module driving technique can be summarized as follows:

step 1: the central processing unit 15 which hosts the driving software sends a command to the wavelength selector so that it selects a new excitation wavelength, step 2: the wavelength selector executes the preliminarily received command and shifts the optical interference filter disk of the module 13 so as to select the excitation wavelength (or range of excitation wavelengths) desired.

step 3: the central processing unit 15 then sends out a command to the image-capturing module 14 to make it take an image of the sample subjected to the selected excitation wavelength, step 4: the image-capturing module 14 executes the command and acquires an image (or a series of images) of the sample.

It must be noted that each of these steps is illustrated in FIG. 1 by a circle in which the number of the concerned step is inscribed. The same convention is adopted in the subsequent figures relating to the present invention (described in detail under section 5 here below in the description).

These four steps are reiterated as many times as necessary so that the sample can be imaged for other excitation wavelengths. An iteration of the above four steps therefore corresponds to the capturing of an image or a series of images of the sample subjected to radiation in a given excitation wavelength.

It must be noted that it is also possible to change the position in space of the sample 16 or that of the objective of the microscope during the acquisition of the images, especially along the optical axis of the microscope $12_1$ (axis Z) in order to image the sample in depth. Combined with multifocal microscopy, this process enables the in-depth imaging of different optical sections of the sample by eliminating fluorescence (optical noise source) outside the observed plane. This therefore requires an additional driving of the functional module $12_1$.

3.2 Technical Problem of the Invention

The present technique for driving functional modules by means of a dedicated software program still has many drawbacks. This technique indeed requires that the image-capturing and wavelength-selection modules should be activated successively by means of one-way commands sent in a centralized manner by the driving software. This means that the driving of the modules is relatively slow and relatively lacking in robustness when coping with problems of synchronization if any.

In addition, the fact of controlling the optical filter disk by means of the driving software combined with the relatively low speed of rotation of this disk slows down the pace of acquisition of the images.

Besides, in using this configuration, the inventors have become aware of the presence of spectral leakage from the laser source in the emission channel. This is not an optimal state of affairs. Indeed, owing to the intrinsic characteristics of presently used filters, it is not always possible to filter out all the undesired wavelengths coming from the excitation laser source (especially the infrared source). These undesired wavelengths are found in the sample and could cause it to deteriorate, and are also found in the image sensor, causing problems in the observation of the fluorescence of the sample.

4. SUMMARY OF THE INVENTION

One particular embodiment of the invention proposes a method for driving a plurality of functional modules included in a multi-wavelength microscopy imaging device configured to take a plurality of image shots of a sample subjected to different excitation wavelengths, said imaging device comprising at least one first functional module and one second functional module, adapted respectively to performing a first function and a second function. The first functional module is a wavelength-selection module and the first function consists in making a selection of at least one excitation wavelength for the sample and the second functional module is an image-capturing module and the second function consists in taking an image shot of the sample. The method is such that it includes at least one iteration of the following steps:
a) sending a first driving signal to the second functional module when the first functional module has performed the first function;
b) the second functional module triggers said function upon reception of the first driving signal;
c) sending a second driving signal to the first functional module when the second functional module has performed said second function;
d) the first functional module triggers said first function upon reception of the second driving signal.

The principle of the invention relies on the implementation of a mechanism of two-way exchange of driving signals between the modules themselves to activate the function proper to them. A driving signal received by a module is interpreted as a signal for activating the function associated with it. Thus, by a "ping pong game" between the modules, the method according to the invention enables each functional module to be commanded in succession without using a central software and decision-making entity as is the case in the prior art. Thus, a driving signal received by the first module triggers a selection of a wavelength or a range of wavelengths and a driving signal received by the second module triggers an action of taking an image shot of the sample for the wavelength selected by the first module. This asynchronous and parallel approach therefore has the effect of improving the speed of acquisition of the images by the image-capturing module as well as the robustness of the multi-wavelength imaging process. The number of iterations of the steps a) to d) can be defined according to the number of excitation wavelengths to which the sample must be exposed (for example the number of iterations can be chosen to be equal to the number of excitation wavelengths selected, namely one image shot of the sample for each selected wavelength).

According to one particular embodiment, the step a) for sending a first driving signal is performed by the first functional module and the step b) for sending a second driving signal is performed by the second functional module.

Since the modules are driven by the functional modules themselves, this variant removes the need for using a dedicated device to implement the driving process. This variant is therefore simple and costs little to implement.

According to one particular characteristic, the microscopy imaging device comprises at least one third functional module adapted to performing a third function, the method furthermore comprising the following steps:
e) the first functional module sends a third driving signal to the third functional module upon reception of the second driving signal;
f) the third functional module triggers the activation of said third function upon reception of the third driving signal;
g) the third functional module sends a fourth driving signal to the first functional module when the third functional module has performed said third function;
the step a) for sending of a first driving signal to the second functional module being carried out when the first functional module has performed said first function and upon reception of the fourth driving signal.

Thus, the method according to the invention offers the possibility of driving at least one third functional module within the multi-wavelength imaging device in a relatively simple way. To this end a mechanism for exchanging two-way signals is implemented between the first and third functional modules to enable said modules to be driven in succession (as in a ping pong game) without using a central software entity.

The additional condition for the first module to send a driving signal to the second module to trigger the second function is that it should have received a driving signal from the third module, this signal being interpreted by it as a signal for activating the sending of a driving signal to the second module.

According to one particular aspect of the invention, an iteration of the steps e) to g) is done following the steps a) to d) at a frequency equal to 1/n with n being the number of excitation wavelengths to which the sample is subjected, the number of interactions of the steps a) to d) being equal to n.

Thus, it is not necessary to trigger the function of the third module at each iteration of the steps a) to d) (in other words whenever the function of the first and second modules are activated). This offers greater flexibility in the driving of a plurality of modules.

According to one alternative embodiment, the step a) for sending a first driving signal and the step b) for sending a second driving signal are performed by a dedicated logic module independent of the first and second functional modules.

This alternative embodiment has the advantage of being adaptable to any architecture whatsoever that may be dictated by the imaging device.

According to one particular characteristic, the imaging device comprises at least one third functional module adapted to performing a third function, the method furthermore comprising the following steps:
when the second functional module has performed said second function, the dedicated logic module sends a third driving signal to the third functional module at the same time as the step for sending the second driving signal to the first functional module;

the third functional module triggers the activation of said third function upon reception of the third driving signal;

the third functional module sends a fourth driving signal to the dedicated logic module when the third functional module has performed said third function;

the step a) for sending a first driving signal to the second functional module being carried out when the first functional module has performed said first function and upon reception of the fourth driving signal.

Thus, the method according to the invention offers the possibility of driving at least one third functional module. To this end, a mechanism for exchanging two-way signals is implemented between the dedicated logic module and the third functional module to enable a successive driving of the functional modules between themselves via the logic module.

According to one particular aspect, the third functional module is a module for positioning the sample and the third function consists in effecting a shifting of the sample in at least one direction of space.

This characteristic enables the performance of a three-dimensional acquisition in addition to a multi-wavelength acquisition. It is thus possible to plan for activating the function of the third module (shifting of the sample in space) only once in every n excitation wavelengths in order to optimize the number of exchanges of driving signals between modules. The sample can be shifted along the optical axis of the image capturing-module, for example in order to carry out a 3D acquisition of the sample.

Another embodiment of the invention proposes a system for driving a plurality of functional modules included in a multi-wavelength microscopy imaging device configured to take a plurality of image shots of a sample subjected to different excitation wavelengths, said imaging device comprising at least one first functional module and one second functional module adapted respectively to performing a first function and a second function, the system being characterized in that it comprises:

means for sending out a first driving signal to the second functional module activated when the first functional module has performed said first function;

means for triggering said first function, activated upon reception of a second driving signal received from the second functional module;

means for triggering said second function, activated upon reception of the first driving signal received from the first functional module;

means for sending out the second driving signal to the first functional module, activated when the second functional module has performed said second function.

According to one particular characteristic, the first functional module is a wavelength-selection module and the first function consists in making a selection of at least one excitation wavelength for the sample; the second functional module is an image-capturing module and the second function consists in taking an image shot of the sample.

According to one particular characteristic, the imaging device comprises at least one third functional module adapted to carrying out a second function, the system furthermore comprising:

means for sending out a third driving signal to the third functional module, activated upon reception of the second driving signal;

means for triggering said third function, activated upon reception of third driving signal.

According to one particular characteristic, the third functional module is a module for positioning the sample and the third function consists in positioning the sample in at least one direction of space.

According to one particular aspect, the wavelength selection module comprises a set of two optical prisms disposed on either side of a slot mounted so as to be mobile in translation and controlled by the second driving signal sent by the second functional module to make a selection of at least one excitation wavelength.

This characteristic makes it possible to provide a wavelength selector adapted to fluorescence microscopy that is faster (by a few tens of milliseconds) than the prior-art devices such as the filter wheel and the tunable filter systems. In addition, when they are used with a laser supercontinuum, the systems of selection by acousto-optic modulator generate critical spectral leakages and are therefore, unlike the invention, not suited to fluorescence microscopy. This structural configuration is particular well-suited to hardware driving. The improved speed of the wavelength-selection process combined with the driving without any centralized software entity (synergy effect) provides a multi-layer wavelength imaging system that is fast and more robust than the imaging systems of the prior art.

5. LIST OF FIGURES

Other features and advantages of the invention shall appear more clearly from the following description, given by way of an indicative and non-exhaustive example and from the appended drawings of which.

6. DETAILED DESCRIPTION

In all the figures of the present document, identical elements and steps are designated by a same numerical reference.

The general principle of the invention consists in implementing a mechanism for the two-way exchange of driving commands between the functional modules themselves (rather than a centralized one-way driving module controlled by a dedicated software program) with asynchronous and/or simultaneous movements of certain modules followed by checkpoints at certain instants of execution and making it possible to offer a multi-wavelength imaging system that is fast and robust. These checkpoints are made not by the software program executed on the computer as in the prior art but via one or more controllers respectively attached to certain functional modules and/or via one dedicated controller.

Figure 2:
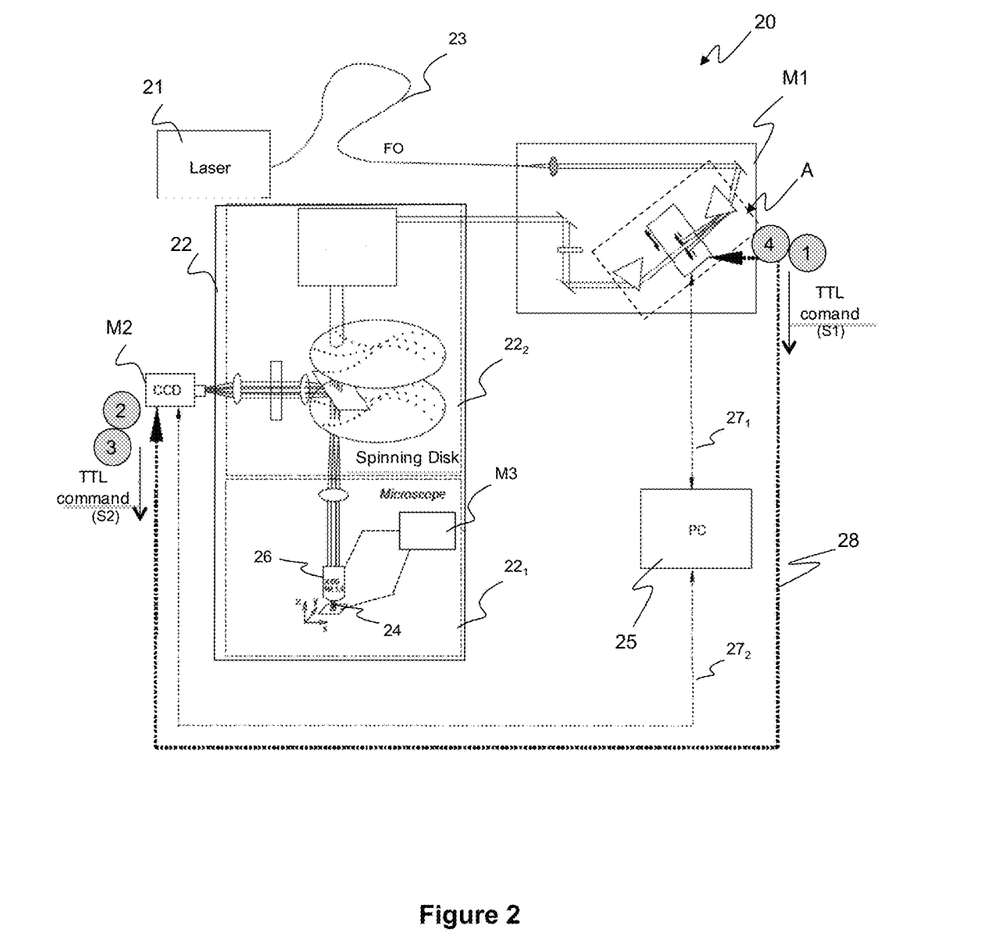
FIG. 2 shows an example of a multi-wavelength multifocal imaging device in which there is implemented the method of driving according to one particular embodiment of the invention.

FIG. 2 shows an example of a multifocal, multi-wavelength imaging device in which the driving method according to one particular embodiment of the invention can be implemented.

The purpose of the imaging device 20 is to image a sample 24 subjected to different excitation wavelengths. It comprises a laser light source 21 coupled, via an optical fiber 23 (denoted "FO" in the figure), to a wavelength-selection system (denoted as M1), itself coupled in free space to a multifocal microscope 22. The light source 21 produces an excitation white laser light called a "supercontinuum" light pulsed at an impulse rate of the order of a few picoseconds intended to illuminate the sample 24 to be observed. The multifocal microscope 22 is formed by an imaging module $22_1$ cooperating with a confocal spinning disk $22_2$.

The imaging device 20 comprises the following functional modules:
  a wavelength-selection module M1, adapted to performing a first function (denoted as F1 below) which consists in selecting a wavelength or a specific range of wavelengths by shifting a mobile slot 40 contained between two optical prisms 41 and 42 (the principle of which is described in detail further below with reference to FIG. 7), to excite the sample 24;
  an image-capturing module 22, for example a CCD (Charge-Coupled Device) or CMOS (Complementary Metal Oxide Semiconductor) type camera, adapted to performing a second function (denoted as F2 below) which consists in capturing an image of the sample 24;
  a module for shifting the sample M3, adapted to performing a third function (denoted below as F3) consisting in shifting the sample 24 or the objective of the microscope in at least one direction of space along X, Y and/or Z.

Example of Driving with Two Functional Modules

Figure 3:
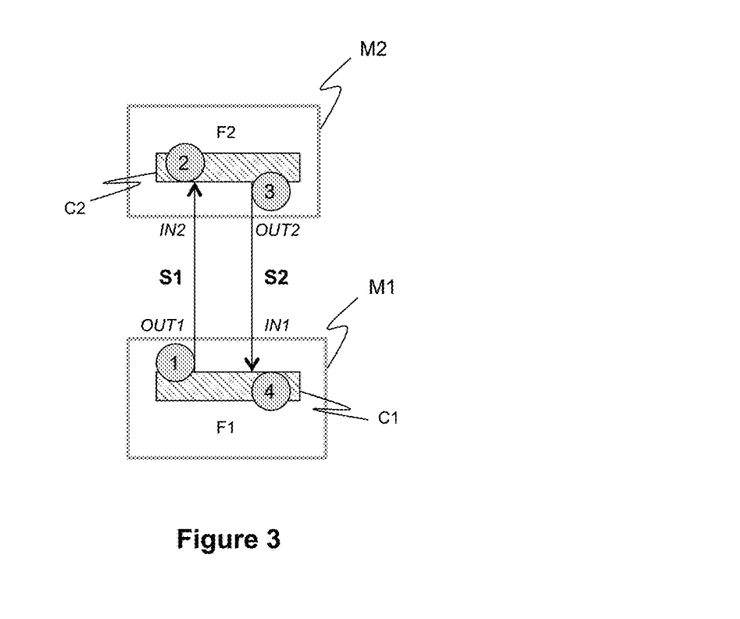
FIG. 3 is a functional block diagram illustrating the principle of the driving method according to a first embodiment of the invention.
Figure 4:
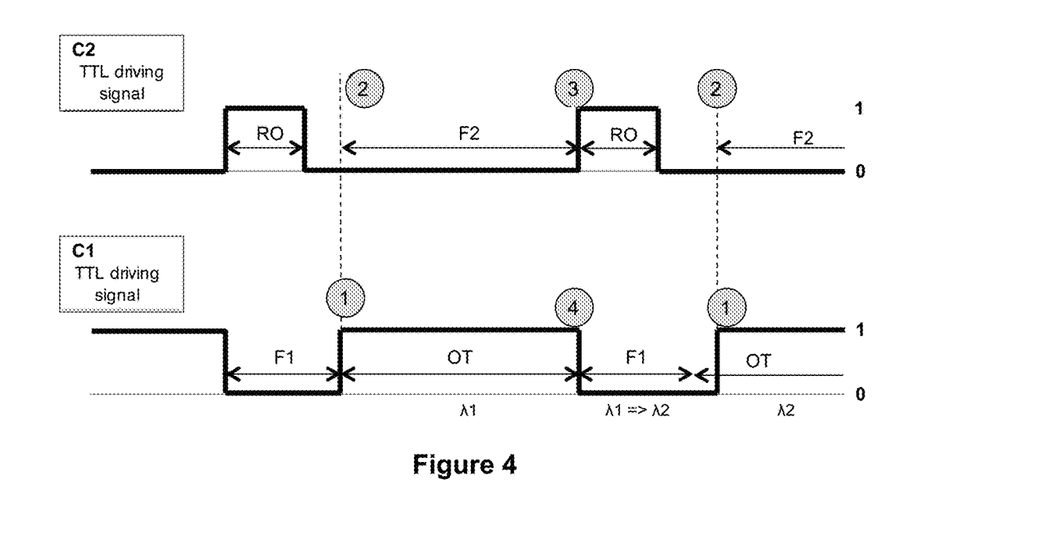
FIG. 4 is a timing diagram representing the progress in time of the driving signals exchanged between the functional modules illustrated in FIG. 3.

Here below, referring to FIGS. 3 and 4, we present the principle of the driving method according to a first particular embodiment of the invention, in which a driving of two functional modules M1, M2 is performed. FIG. 3 is a functional block diagram of the system for driving the functional modules M1 and M2, and FIG. 4 is a timing diagram showing the progress in time of the driving signals exchanged between the functional modules M1 and M2.

The driving method presented here is implemented to image a sample subjected to two distinct excitation wavelengths $\lambda 1$ and $\lambda 2$. The number of wavelengths to which the sample can be subjected during multicolor acquisition is herein deliberately limited purely as a pedagogical description so as not to excessively to burden the figures and the associated description. Naturally, a greater number of wavelengths can be used if necessary without departing from the framework of the invention.

The wavelength-selection module M1 and the image-capturing module M2 respectively comprise the input-output controllers C1 and C2 which manage the activities of their respective module and execute the transfer of the data:
  the controller C1 manages the performance of the function F1 namely the selection of an excitation wavelength for the sample (by shifting the mobile slot 40 on the excitation wavelength to be used)
  the controller C2 manages the performance of the function F2, namely capturing images or taking image shots of the sample.

A macro-command containing a sequence of program code instructions to implement the method is loaded by the controller C1 of the module M1 from the central processing unit 25, via the software communications link $27_1$, to be executed in the module M1. The macro-command is embedded in the controller of the module M1.

The macro-command is defined so that the controller C1 of the module M1 triggers the selection of a new wavelength whenever it receives a TTL driving signal and sends out a TTL driving signal whenever it has finished performing this function.

Before executing the macro-command, the image-capturing module M2 is started in continuous trigger mode for acquisition by external signals from the central processing unit 25 via the controller C2 and the software communications link $27_2$. It is thus configured so as to acquire an image whenever it receives a TTL driving signal.

When the method is initialized, the controller C1 of the module M1 selects a first excitation wavelength $\lambda 1$ in shifting the mobile slot 40 between the two optical prisms 41 and 42 until it is positioned on the excitation wavelength $\lambda 1$. Then, the multicolor acquisition starts and is driven solely by the TTL signals exchanged between the modules M1 and M2.

The logic level 1 signifies the sending of a high TTL driving signal by one of the functional modules and the logic level 0 signifies that the functional module in question is sending a low TTL driving signal. At a step 1, the controller C1 of the module M1 sends a high TTL driving signal S1 to the controller of the module M2 when two conditions are met: on the one hand, the excitation wavelength $\lambda 1$ has been selected by the controller C1 (in the figure, this condition is called OT for "on target" which means that the slot 40 is in position) and on the other hand the TTL driving signal S2 of the controller C2 is low when the processing of the image shot is terminated (denoted in the figure as RO for "Read Out").

In a step 2, the controller C2 of the module M1 triggers the taking of an image shot of the sample, when it receives the high TTL driving signal S1 from the controller C1 (function F2). The TTL driving signal S1 received by the controller C2 is interpreted as being a signal for triggering the taking of an image shot of the sample.

In a step 3, the controller C2 sends a high TTL driving signal S2 to the controller of the module M1 when the controller C2 has taken the image shot of the sample exposed to the wavelength $\lambda 1$. In parallel, the controller C2 processes the image shot (denoted in the figure as RO for Read Out).

In a step 4, the controller C1 triggers the selection of a new excitation wavelength $\lambda 2$ when it receives the high TTL driving signal S2 from the controller C2 (function F1). The high TTL driving signal S2 received by the controller C1 is interpreted as being a signal for triggering a selection of a new wavelength.

These two-way TTL driving signals between the modules M1 and M2 are conveyed by wire communication means 28 such as for example a coaxial cable with BNC connectors.

The successive triggering of the functions of the modules M1 and M2 by means of TTL driving commands exchanged directly between the modules themselves (by analogy with a game of ping pong) ensures the driving of the modules without using the central processing unit 25, thus improving the speed of acquisition of the images by the module M1. Each TTL driving signal received is interpreted by the module as a command for triggering action.

The number of iterations of the steps 1 to 4 presented above can be defined as a function of the number of excitation wavelengths to which the sample must be exposed. In the example presented here, the number of excitation wavelengths to which the sample must be exposed is equal to 2 ($\lambda 1$, $\lambda 2$). The steps 1 to 4 should therefore be reiterated twice in order to obtain two shots of the sample, each made with a distinct excitation wavelength. It must be noted that the events do not necessarily take the same time at each cycle. This is an advantage because it eliminates the time limits needed to impose regularity in the acquisition of the images.

Example of Driving with Three Functional Modules

Figure 5:
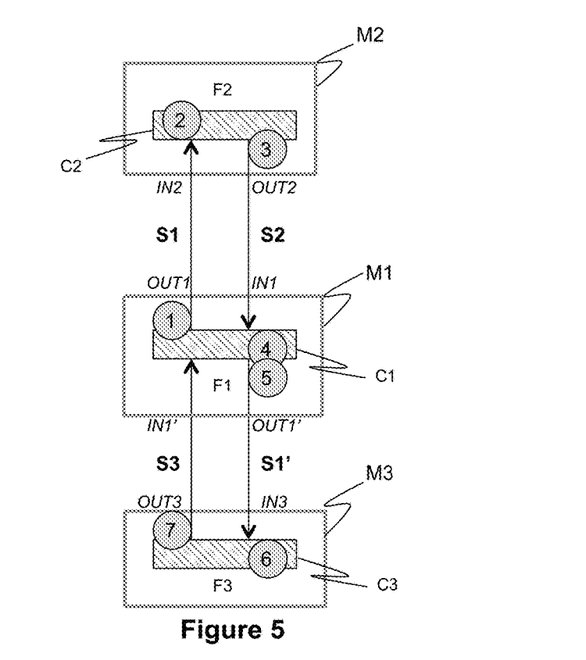
FIG. 5 is a functional block diagram illustrating the principle of the driving method according to a second embodiment of the invention.
Figure 6:
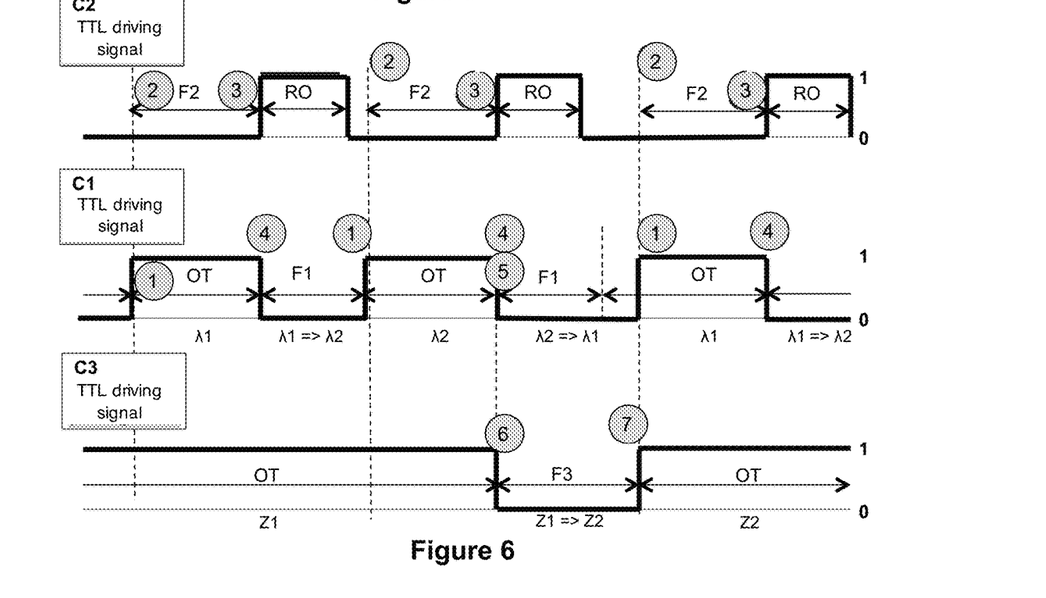
FIG. 6 is a timing diagram representing the progress in time of the driving signals exchanged between the functional modules illustrated in FIG. 5.

Here below, referring to FIGS. 5 and 6, we present the principle of the method of driving according to a second particular embodiment of the invention in which a driving of three functional modules M1, M2, M3 is carried out. FIG. 5 represents a functional block diagram of the system for driving functional modules M1, M2 and M3 and FIG. 6 is a timing diagram showing the progress in time of the driving signals exchanged between the functional modules M1, M2, M3. The wavelength-selection module M1, image-capturing module M2 and sample-shifting module M3 respectively comprise the input-output controllers C1, C2 and C3 which manage the activities of their respective modules and execute the transfer of the data:

the controller C manages the performance of the function F1, namely the selection of an excitation wavelength for exciting the sample (by shifting the mobile slot on the planned excitation wavelength), the controller C2 manages the performance of the function F2, namely capturing an image or taking an image shot of the sample, the controller C3 manages the performance of the function F3, namely the shifting of the sample along the axis Z (corresponding to the optical axis of the microscope 22$_1$).

A macro-command containing the sequence of program code instructions to implement the method is loaded by the controller C1 of the module M1 from the central processing unit 25, via the software communications link 27$_1$ to be executed in this module M1.

The macro-command is defined in such a way that the controller C1 of the module M1 triggers the selection of a new wavelength whenever it receives a TTL driving signal and sends out a TTL driving signal whenever it has completed the performance of this function.

Before executing the macro-command, the image capturing module M2 is started in continuous trigger mode for acquisition by external signal from the central processing unit via the controller C2 and the software communications link 27$_2$. It is thus configured so as to acquire an image whenever it receives TTL driving signal.

When the method is initialized, the controller C1 of the module M1 selects a first excitation wavelength $\lambda 1$ in shifting the mobile slot 40 between the two optical prisms 41 and 42 until it is positioned on the excitation wavelength $\lambda 1$. The controller C3 of the module M3 shifts the sample until it is situated in a first position Z1. Then, the multicolor acquisition starts and is driven solely by the TTL signals exchanged between the three modules M1, M2, M3.

In a step 1, the controller C1 of the module M1 sends a high TTL driving signal S1 to the controller of the module M2 when three conditions are met: firstly, the excitation wavelength $\lambda 1$ has been selected by the controller C1 (denoted in the figure as OT or On Target, meaning that the slot 40 is in position), secondly, the TTL driving signal S2 of the controller C2 is low when the processing of the shot denoted as RO or Read Out in the figure) is terminated and finally the TTL driving signal S3 of the controller C3 is high when the shift along Z is terminated (denoted in the figure as OT for On Target). Thus, the functions F1 and F3 are executed in parallel independently and asynchronously. The process for controlling the different functions works as a "checkpoint" system (i.e. according to a mechanism for verifying checkpoints) at a determined step of the sequence without any synchronization of the functions. In this context, the method works as speedily as possible.

In a step 2, the controller C2 of the module M2 triggers an image shot of the sample when it receives the high TTL driving signal S1 of the controller C1 (function F2). The high TTL driving signal S1 received by the controller C2 is interpreted as being a signal for triggering an image shot of the sample.

At a step 3, the controller C2 sends a high TTL driving signal to the controller of the module M1 when the controller C2 has taken the image shot of the sample exposed to the wavelength $\lambda 1$. At the same time, the controller C2 carries out a processing of the image shot (denoted in the figure as RO or Read Out).

In a step 4, the controller C1 triggers the selection of a new excitation wavelength $\lambda 1$ when it receives the high TTL driving signal S2 from the controller C2 (function F1). The high TTL driving signal S2 received by the controller C1 is interpreted as being a signal for triggering a selection of a new wavelength.

The steps 1 to 4 above are reiterated twice successively so as to acquire a first image shot of the sample for the excitation wavelength $\lambda 1$ and a second image shot of the sample for the excitation wavelength $\lambda 1$ for the position Z1 of the sample (first optical section).

In a step 5, the controller C1 of the module M1 sends a new high TTL driving signal S', but this time it sends it to the controller of the module M3 upon reception of the high TTL driving signal S2 from the controller C2. At the same time, the controller C1 triggers a selection of a new excitation wavelength, namely $\lambda 1$ ($\lambda 2 \Rightarrow \lambda 1$).

In a step 6, the controller C3 of the module M3 triggers a shift of the sample until it is situated in a second position Z2 (at the initialization of the method, the sample had been in a position Z1) upon reception of the high TTL driving signal S1' sent by the controller C1. Thus, the two functions F1 and F3 are executed in parallel independently and asynchronously.

At a step 7, the controller C3 of the module M3 sends a high TTL driving signal S3 to the controller C1 when the controller C3 has terminated the shifting of the sample, this sample being situated in the position Z2.

Then the steps 1 to 4 are again reiterated twice. However, this is done under such the following conditions: the controller C1 has, firstly, carried out the selection of the excitation wavelength $\lambda 1$ and, secondly, received the high TTL driving signal S3 sent by controller C3. This second condition, thus verified, ensures that the sample 24 is truly situated in the position planned (Z2 in this case) before launching a new iteration of the steps 1 to 4.

Acting again on the basis of the principle that an imaging operation is done for each excitation wavelength $\lambda 1$, $\lambda 2$, the steps 1 to 4 above are reiterated twice in succession so as to acquire a first image shot of the sample for the excitation wavelength λ1 and a second shot of the sample for the excitation wavelength λ2, for the position Z2 (second optical section).

In general, an iteration of the steps 5, 6 and 7 is considered to be done at a frequency equal to 1/n with n being the number of wavelengths to which the sample is subjected, the number of iterations of the steps 1 to 4 being equal to n.

The addition of the module M3 to the driving process is of genuine interest since it enables the performance of 3D microscopy driven at ultra high speed, in addition to multi-wavelength microscopy. Indeed, the functions are executed independently and asynchronously without passing through the software entity 25 and without imposing time limits of execution to make sure that the functions have been truly performed. Multifocal microscopy makes it possible to image optical sections of a sample by physically (through the pinholes of the spinning disk $22_2$) eliminating the fluorescence observed outside the plane (which is a source of optical noise). It is therefore possible, by shifting the sample (or the head of the microscope 26) along the optical axis of the microscope (axis Z) to image the sample in depth. The term used here below in this document will be "multi-z microscopy".

The driving method represented here is implemented to image a sample subjected to two distinct excitation wavelengths λ1, λ2 and two distinct positions Z1, Z2 along the axis Z. The number of wavelengths as well as the number of positions occupied by the sample is herein deliberately limited as a purely pedagogical description so as not to excessively burden the figures and the associated description. Naturally a greater number of wavelengths and/or positions of the sample along the axis Z can be planned without departing from the framework of the invention.

According to one alternative embodiment, it can be provided that the module M3 will be configured to shift not the sample but the head of the microscope 26 relative to the sample along the axis Z.

According to another variant of the invention, it can be planned in the method to shift the sample 24 or the head of the microscope 26 not only along the axis Z to ensure the 3D microscopy function but also along the X and Y axes to enable a spatial microscopic analysis of the phenomenon.

As for the driving system illustrated in FIG. 3:
the controller C1 of the functional module M1 comprises:
    means OUT1 for sending the driving signal S1 to the functional module M2 activated when the functional module M1 has performed its function F1;
    means IN1 for receiving the driving signal S2 sent by the functional module M2;
    means for triggering the function F1 activated upon reception of the driving signal S2 by the reception means
the functional module M2 comprises:
    means OUT2 for sending the driving signal S2 to the functional module M1, activated when this functional module M2 has performed its function F2;
    means IN2 for receiving the driving signal S1 sent by the functional module M1;
    means for triggering the function F2 activated upon reception of the driving signal S1 by the reception means IN2.
With regard to the driving system illustrated in FIG. 5:
the controller C1 of the function M1 furthermore comprises:
    means OUT1' for sending the driving signal S1' to the functional module M3;
    means IN1' for receiving the driving signal S3 sent by the module M3;
the functional module M3 comprises:
    means OUT3 for sending the driving signal S3 to the functional module M1 activated when the functional module M3 has performed its function F3;
    means IN3 for receiving the driving signal S1' sent by the module M1;
    means for triggering the activated function F3 upon reception of the driving signal S1 by the reception means IN3.

A simplified example of instructions of the macro-command embedded in the controller of the module M1 is presented below:

| | |
|---|---|
| Move | move to first wavelength (λ1) |
| Wait IN1 = 0 | |
| Wait On target | |
| Send OUT 1 = 1 | trigger an image shot |
| Wait IN1 = 1 | |
| Move | move to second wavelength (λ2) |
| Wait IN1 = 0 | |
| Wait On target | |
| Send OUT 1 = 1 | trigger an image shot |
| Wait IN1 = 1 | |
| Send OUT1' = 1 | shift sample to second position (Z2) |
| Move | move to first wavelength (λ1) |
| Wait On target | |
| Wait IN1 = 0 | |
| Wait IN1' = 1 | |
| Send OUT1 = 1 | trigger an image shot |

Figure 7:
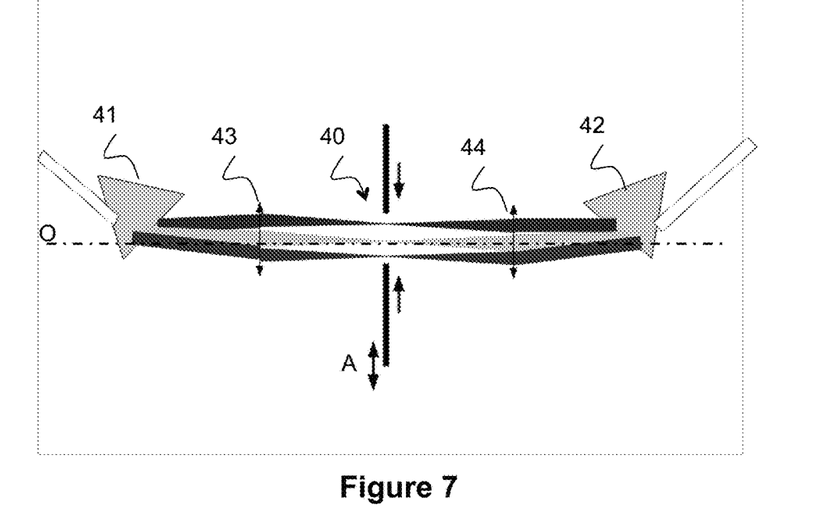
FIG. 7 presents the structural details of a wavelength-selection module according to one particular embodiment of the invention.

FIG. 7 presents the structural details of a wavelength-selection module M1 according to one particular embodiment of the invention.

The module M1 represented here by the arrow A comprises a set of two optical prisms 41, 42 disposed on either side of a slot 40 mounted so as to be mobile in translation on a high-speed translation plate. The two prisms are each associated with an optical lens 43, 44 respectively. The optical prisms 41, 42 and lenses, 43, 44 form an optical assembly having an optical axis O.

The slot 40 is controlled by the input-output controller C1 for the selection of a given wavelength. A TTL driving signal received by the input-output controller C1 triggers the shifting of the slot perpendicularly to the optical axis O.

According to a first embodiment, the slot is formed by a set of two separate strips of fixed length mounted so as to be mobile in translation perpendicularly to the optical axis O. This enables the adjustment of the position of the slot relative to the optical axis as a function of the wavelength or range of wavelengths desired.

According to a second embodiment, the slot is formed by a set of two separate strips, each strip being mounted so as to be independently mobile in translation perpendicularly to the optical axis O so as to adjust both the width and the position of the slot relative to the optical axis O. This offers the possibility of selecting a spectral band of adjustable width (for example 3.5 to 300 m) to excite the sample.

These structural characteristics provide a wavelength selector, adapted to fluorescence microscopy, that is faster (by about some tens of milliseconds) than the prior art selectors such as the filter wheel or tunable filter systems. In addition, when used with a supercontinuum laser, the systems of selection by acousto-optical modulator generate critical spectral leakages and are therefore not suited to fluorescence microscopy unlike the present invention. In the embodiments of the invention, the improved speed of the process of selection of wavelengths combined with the system of driving without software provides a multi-wavelength imaging system that is faster and more robust than the imaging systems of the prior art.

In the particular embodiments discussed above, the macro-command is embedded in the wavelength selection module. It is clear than many other embodiments of the invention can be envisaged. It is possible especially to provide for the embedding of this macro-command in another functional module, in the positioning module M3 for example, without departing from the framework of the invention or again in an external input-output module based on a dedicated micro-controller as illustrated below with reference to FIGS. 8A and 8B.

Example of Driving Carried Out by a Dedicated Module

Figure 8A:
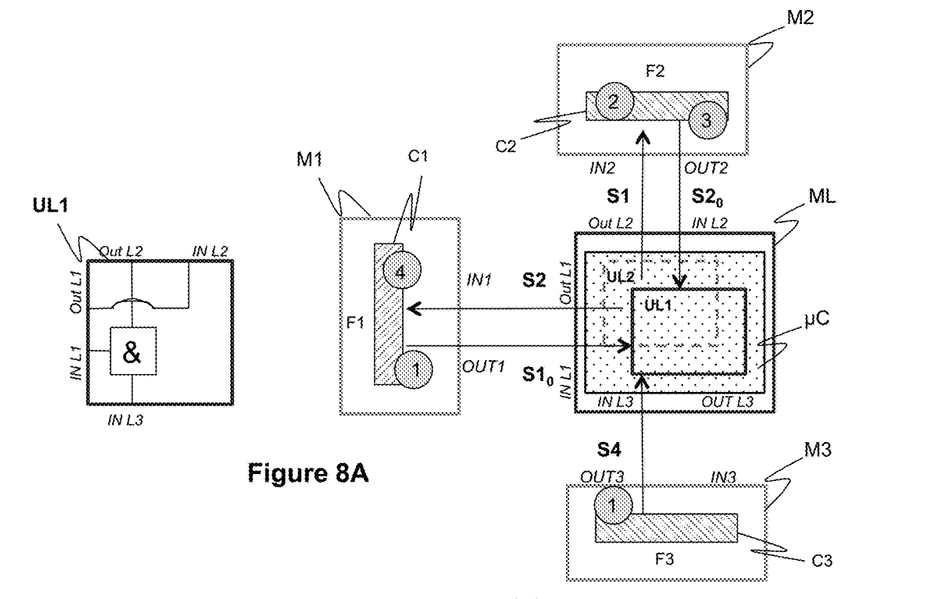
FIGS. 8A and 8B present functional block diagrams illustrating the principle of the method of driving according to a third embodiment of the invention.
Figure 8B:
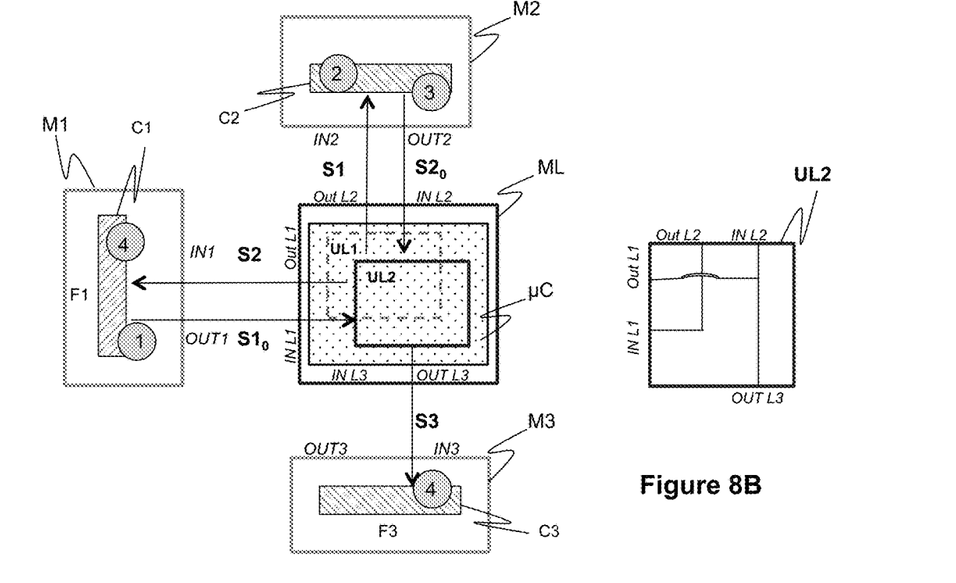

We now present a third particular embodiment of the invention in which three functional modules M1, M2, M3 are driven by means of a driving logic module referenced ML ("module logique" or "logic module"). The logic module ML is equipped with a dedicated microcontroller (denoted as µC) responsible for executing the driving method.

In this embodiment, the microcontroller µC comprises a succession/alternation of logic units, each logic unit implementing one group of specific steps in a complex acquisition. In the present case, the functional modules M1, M2 and M3 work independently with an input signal to activate their function F1, F2 and F3 respectively and an output signal when their respective function is completed. Thus, a single logic unit makes it possible to implement the checkpoints. To carry out a multicolor, multi-z sequence as presented further above in the embodiment, two logic units are necessary:

a first logic unit referenced UL1, is used to activate the function F1 alone (change of wavelength) after having actuated the function F2 (taking an image), a second logic unit referenced UL2 is used to actuate the functions F1 (change of wavelength) and F3 (change of position z) at the same time asynchronously and in parallel after having actuated the function F2 (taking an image).

When the method is initialized, the controller C1 of the module M1 selects a first excitation wavelength $\lambda 1$ in shifting the mobile slot 40 between the two optical prisms 41 and 42 until this slot positioned on the excitation wavelength $\lambda 1$. The controller C3 of the module M3 shifts the sample until it is situated in a first position z1. Then the multicolor acquisition starts and is driven by the TTL signals exchanged between the three modules M1, M2 and M3 by means of logic units UL1, UL2. The signals are successively relayed by the logic units UL1 and UL2.

In one particular embodiment, the logic units UL1 and UL2 are pre-wired, as illustrated in a simplified way in the figures, so that they can carry out logic operations enabling the driving of the three modules M1, M2, M3.

The logic unit UL1 is used by the micro-controller to execute a first group of steps illustrated in FIG. 8A.

In a step 1, the controller C1 of the module M1 sends a high TTL driving signal $S1_0$ to the logic unit UL1 when the selection of the excitation wavelength $\lambda 1$ has been made by the controller C1. Initially, the controller C3 of the module M3 sends a high TTL driving signal S4 to the logic unit UL1 when the shifting of the sample to the position Z1 has been done by the controller C3.

In a step 2, the logic unit UL1 implements a checkpoint. It sends a high TTL driving signal S1 to the controller of the module M2 when three conditions are met: reception of the high TTL driving signal $S1_0$ coming from the module M1, reception of the TTL driving signal S4 coming from the module M3 (by means of the AND logic gate symbolized by "&" in the figure) and checks that the TTL driving signal $S2_0$ of the controller C2 is low confirming that the processing of the image shot is terminated. The controller C2 of the module M2 then triggers an image shot of the sample (Function F2) when it receives the high TTL driving signal S1 from the logic unit UL1 which means that the two modules M1 and M2 have each performed their function asynchronously and that the module M2 is ready for this imaging operation. The high TTL driving signal S1 received by the controller C2 is interpreted as being a signal for triggering an image shot of the operation.

In the step 3, the controller C2 sends a high TTL driving signal $S2_0$ to the logic unit UL1 when the controller C2 has taken the image shot of the sample exposed at the wavelength $\lambda 1$ and in the position Z1. In parallel, the controller C2 carries out a processing of the image shot.

In a step 4, the logic unit UL1 sends a high TTL driving signal S2 to the controller of the module M1 upon reception of the high TTL driving signal $S2_0$. The controller C1 then triggers the selection of a new excitation wavelength $\lambda 1$ when it receives the high TTL driving signal S2 from the logic unit UL1 (Function F1). The high TTL driving signal S2 received by the controller C1 is interpreted as being a signal for triggering a selection of a new wavelength.

It must be noted that in this particular example:

the TTL signal $S1_0$ received by the unit UL1 is interpreted by this unit as being a signal for triggering the dispatch of the TTL driving signal S1 to the module M2. The logic unit UL1 a "relays" the high TTL signal given by the controller C1 to the controller C2 only after having implemented a logic checkpoint.

the TTL signal $S2_0$ received by the unit UL1 is interpreted by this unit as being a signal for triggering the dispatch of the TTL driving signal S2 to the module M1. This logic unit UL1 "relays" the high TTL signal given by the controller C2 to the controller C1 immediately and without processing.

The logic unit UL2 is used by the micro-controller for the execution of a second group of steps illustrated in FIG. 8B. The logic unit UL2 is executed once the execution of the unit UL1 is terminated.

In a step 1, the controller C2 of the module M1 sends a high TTL driving signal $S1_0$ to the logic unit UL2 when the selection of the excitation wavelength $\lambda 1$ has been done by the controller C1.

In a step 2 the logic unit UL2 implements a checkpoint. It sends a high TTL driving signal S1 to the controller of the module M2 when two conditions are met: reception of the TTL driving signal $S1_0$ coming from the module M1 and checking that the TTL driving signal $S2_0$ from the controller C2 is low confirming that the processing of the image shot is terminated. The controller C2 triggers an image shot of the sample when it receives the high TTL driving signal S1 from the logic unit UL2, which means that the module M1 has performed its function and that the module M2 is ready for this image shot. The high TTL driving signal S1 received by the controller C2 is interpreted as being a signal for triggering an image shot of the sample.

In a step 3, the controller C2 sends a high TTL driving signal $S2_0$ to the logic unit UL2 when the controller C2 has taken the image shot of the sample exposed at the wavelength $\lambda 1$ and at the position Z1. At the same time, the controller C2 carries out a processing of the image shot.

In a step 4, the logic unit UL2 relays the high TTL driving signal to the controllers C1 and C2 by sending, upon reception of the TTL driving signal $S2_0$, on the one hand a high TTL driving signal S2 to the controller of the module M1 and, on the other hand, a high TTL driving signal S3 to the controller of the module M3. The controller C1 triggers the selection of a new excitation wavelength λ1 when it receives the high TTL driving signal S2 from the logic unit UL2 (Function F1). The high TTL driving signal S2 received by the controller C1 is interpreted as being a signal for triggering a selection of a new wavelength. The controller C3 triggers the selection of a new position Z2 and it receives the high TTL driving signal S3 from the logic unit UL2 (Function F3). The high TTL driving signal S3 received by the controller C3 is interpreted as being the signal for triggering a selection of a new position of the sample along the axis Z.

Then, the execution of the logic units UL1 and UL2 alternate successively for the shots (λ1, Z2) and (λ2, Z2). The sequences of images are driven only by the successive alternation of the logic units which transmit the TTL logic signals between the modules M1, M2 and M3 under conditions.

In other words, as compared with the first and second embodiments described above, the logic module ML acts as a centralized module managing the driving by relaying the TTL driving signals between the different modules. This can be done by means of a simple logic wiring for each group of steps of the driving process. Such a driving module is therefore adaptable to any imaging system in microscopy. It is enough to modify the logic functions of the module by modifying the wiring of this module as a function of the architecture dictated by the imaging system. This driving module ML can furthermore comprise a man/machine interface configured so as to be intuitive for the user who is able to choose the desired acquisition sequence (number of wavelengths, number of images, number of shifts in z, etc.).

In general, the logic module ML is used for the programmatic and coordinated creation of a series of variants of logic units and thus for example for the operating of the sequence presented above by immediately alternating the two logic units UL1 and UL2. This logic module is constituted by a dedicated micro-controller which executes simple micro-commands preliminarily loaded by a computer, enabling the direct or conditional connection of the input/outputs. Thus, it is possible to plan for logic units of any type and immediately load them into the logic modules and thus create sequences of variants to operate any type of acquisition and to do so without departing from the framework of the invention.

The logic module ML has a micro-controller which itself comprises:
means OUT L1 for sending the driving signal S2 to the functional module M1, activated when the functional module M2 has performed its function F2 (i.e. upon reception of the signal $S2_0$);
means IN L1 for receiving the driving signal $S1_0$ sent by the module M1;
means OUT L2 for sending the driving signal S1 to the functional module M2, activated when the functional module M2 has performed its function F1 and when the functional module F3 has performed its function F3 (i.e. upon reception of the signal $S2_0$ and the signal S4);
means IN L2 for receiving the driving signal $S2_0$ sent by the module M2;
means OUT L3 for sending the driving signal S3 to the functional module M3 activated when the functional module M2 has performed its function F2 (i.e. upon reception of the signal $S2_0$);
means INL3 for receiving the driving signal S4 sent by the module 3.

Figure 9:
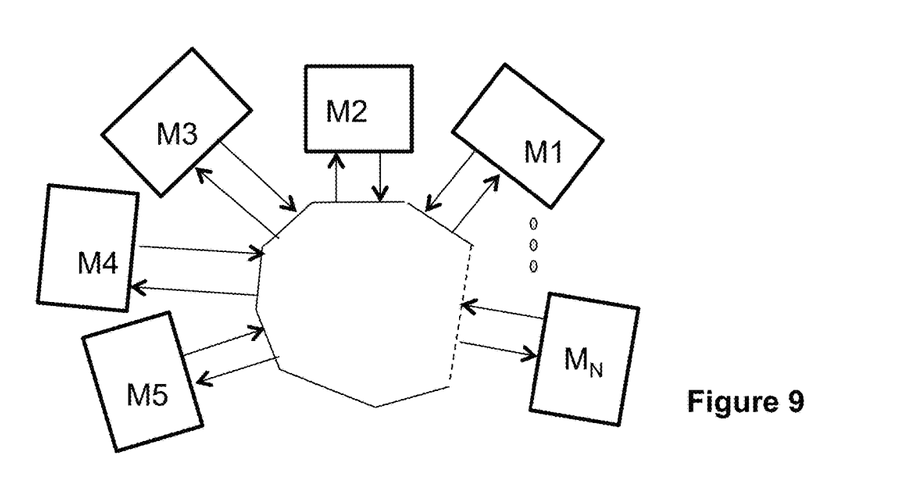
FIG. 9 is a functional block diagram generically illustrating the principle of the driving method according to the invention.

The particular embodiments presented here are used to illustrate a technique of driving the two or three functional modules. As illustrated in FIG. 9, it would be possible to provide for implementing a multi-module driving mode enabling the driving of N functional modules (M1 à $M_N$), with N>3, in extrapolating the principle of the invention described in detail here above with reference to FIGS. 3 to 8 without departing from the framework of the invention, where the driving can be done either by one of the functional modules of the imaging device (according to the principle of FIGS. 3 to 6) or by a dedicated module (according to the principle of FIGS. 8A-8B).

An exemplary embodiment of the present disclosure overcomes the different drawbacks of the prior art.

An exemplary embodiment proposes a driving technique that improves the speed of acquisition of the images as well as the robustness of the multi-wavelength imaging process.

An exemplary embodiment provides a technique of this kind that is relatively simple and costs little to implement.

An exemplary embodiment provides a technique of this kind that reduces the presence of spectral leakages and thus improves the quality of the captured images.

Although the present disclosure has been described with reference to one or more examples, workers skilled in the art will recognize that changes may be made in form and detail without departing from the scope of the disclosure and/or the appended claims.

The invention claimed is:

1. A method comprising:
driving a plurality of functional modules included in a multi-wavelength microscopy imaging device configured to take a plurality of image shots of a sample subjected to different excitation wavelengths, said imaging device comprising at least one first functional module and at least one second functional module, adapted respectively to performing a first function and a second function,
wherein the first functional module is a wavelength-selection module and the first function comprises making a selection of at least one excitation wavelength for the sample
the second functional module is an image-capturing module and the second function comprises taking an image shot of the sample,
and wherein driving the plurality of functional modules comprises at least one iteration of the following acts:
a) sending a first driving signal from the first functional module to the second functional module when the first functional module has performed said first function;
b) the second functional module triggers said second function upon reception of the first driving signal;
c) sending a second driving signal from the second functional module to the first functional module when the second functional module has performed said second function;
d) the first functional module triggers said first function upon reception of the second driving signal.

2. The method according to claim 1, wherein the act a) of sending a first driving signal is carried out by the first functional module and the act b) of sending a second driving signal is performed by the second functional module.

3. The method according to claim 2, wherein the microscopy imaging device comprises at least one third functional module adapted to performing a third function, the method furthermore comprising the following act:

e) the first functional module sends a third driving signal to the third functional module upon reception of the second driving signal;

f) the third functional module triggers the activation of said third function upon reception of the third driving signal;

g) the third functional module sends a fourth driving signal to the first functional module when the third functional module has performed said third function;

and wherein the act a) of sending a first driving signal to the second functional module is carried out when the first functional module has performed said first function and upon reception of the fourth driving signal.

4. The method according to claim 3, wherein an iteration of the acts e) to g) is done following the acts a) to d) at a frequency equal to 1/n with n being the number of excitation wavelengths to which the sample is subjected, the number of interactions of the act a) to d) being equal to n.

5. The method according to claim 1, wherein the act a) of sending a first driving signal and the act b) of sending a second driving signal are carried out by a dedicated logic module independently of the first and second functional modules.

6. The method according to claim 5, wherein the imaging device comprises at least one third functional module adapted to performing a third function, the method furthermore comprising the following acts:

when the second functional module has performed said second function, the dedicated logic module sends a third driving signal to the third functional module at the same time as the act of or sending the second driving signal to the first functional module;

the third functional module triggers the activation of said third function upon reception of the third driving signal;

the third functional module sends a fourth driving signal to the dedicated logic module when the third functional module has performed said third function;

and wherein the act a) of sending a first driving signal to the second functional module is carried out when the first functional module has performed said first function and upon reception of the fourth driving signal.

7. The method according to claim 1, wherein the imaging device comprises at least one third functional module adapted to performing a third function, and wherein the third functional module is a module for positioning the sample and the third function comprises effecting a shift of the sample in at least one direction of space.

8. A system for driving a plurality of functional modules included in a multi-wavelength microscopy imaging device configured to take a plurality of image shots of a sample subjected to different excitation wavelengths, said imaging device comprising at least one first functional module and at least one second functional module, adapted respectively to performing a first function and a second function, the system comprising:

a first controller configured to send out a first driving signal from the first functional module to the second functional module when the first functional module has performed said first function;

a second controller configured to trigger said second function, activated upon reception of the first driving signal received from the first functional module, and the second controller configured to send out a second driving signal from the second functional module to the first functional module, activated when the second functional module has performed said second function;

wherein:

the first controller is configured to trigger said first function, activated upon reception of the second driving signal received from the second functional module;

the first functional module is a wavelength-selection module and the first function comprises making a selection of at least one excitation wavelength for the sample; and the second functional module is an image-capturing module and the second function comprises taking an image shot of the sample.

9. The system according to claim 8, wherein:

the imaging device comprises at least one third functional module adapted to performing a third function;

the first controller is configured to send out a third driving signal to the third functional module, activated upon reception of the second driving signal; and the system includes a third controller configured to trigger said third function, activated upon reception of third driving signal.

10. The system according to claim 9, wherein the third functional module is a module for positioning the sample and the third function comprises positioning the sample in at least one direction of space.

11. The system according to claim 8, wherein the wavelength-selection module comprises a set of two optical prisms disposed on either side of a slot mounted so as to be mobile in translation and controlled by the second driving signal sent by the second functional module to make a selection of at least one excitation wavelength.

* * * * *